US012370127B2

(12) United States Patent
Bear et al.

(10) Patent No.: US 12,370,127 B2
(45) Date of Patent: Jul. 29, 2025

(54) MEDICATION ADHERENCE AND MONITORING SYSTEM AND METHOD

(71) Applicant: MedFreedom LLC, Wellesley, MA (US)

(72) Inventors: David Bear, Wellesley, MA (US); Walter Frankel, Wellesley, MA (US)

(73) Assignee: MedFreedom LLC, Wellesley, MA (US)

( * ) Notice: Subject to any disclaimer, the term of this patent is extended or adjusted under 35 U.S.C. 154(b) by 0 days.

(21) Appl. No.: 18/924,345

(22) Filed: Oct. 23, 2024

(65) Prior Publication Data

US 2025/0134775 A1 May 1, 2025

Related U.S. Application Data

(60) Provisional application No. 63/546,625, filed on Oct. 31, 2023.

(51) Int. Cl.
*A61J 7/04* (2006.01)
*A61J 1/03* (2023.01)
*A61J 7/02* (2006.01)
*G06K 7/14* (2006.01)
*G16H 20/13* (2018.01)

(52) U.S. Cl.
CPC ............. *A61J 7/0481* (2013.01); *A61J 1/035* (2013.01); *A61J 7/02* (2013.01); *G06K 7/1417* (2013.01); *G16H 20/13* (2018.01); *A61J 2200/30* (2013.01); *A61J 2200/70* (2013.01); *A61J 2205/10* (2013.01)

(58) Field of Classification Search
CPC .. A61J 7/0481; A61J 1/035; A61J 7/02; A61J 2200/30; A61J 2200/70; A61J 2205/10; G06K 7/1417; G16H 20/13
See application file for complete search history.

(56) References Cited

U.S. PATENT DOCUMENTS

| 9,779,216 B2 * | 10/2017 | Siegel | G16H 20/13 |
| 11,743,424 B1 * | 8/2023 | Lavin | H04N 7/142 |
| | | | 221/3 |
| 2004/0158350 A1 * | 8/2004 | Ostergaard | G16H 20/13 |
| | | | 700/231 |

(Continued)

OTHER PUBLICATIONS

International Search Report in International Application No. PCT/US2024/052541, dated: Jan. 2, 2025.

*Primary Examiner* — Michael Collins
(74) *Attorney, Agent, or Firm* — Morse, Barnes-Brown & Pendleton, P.C.; Sean D. Detweiler, Esq.

(57) ABSTRACT

A medication adherence and monitoring system and method for use with pill packet dosing is provided. The system is configured to mount on a medication reservoir that stores a stream of pill packets. The system utilizes a processor in conjunction with an optical scanner, to read scannable codes on the stream of pill packets to configure the system and track extraction of the pill packets from the reservoir when they pass by the optical scanner as the pill packets are extracted from the reservoir through an opening in a housing that spans or covers a storage container for the pill packets. The system further provides prompting and feedback for the extraction of the pill packets while monitoring compliance with the dosage schedule for the user.

30 Claims, 10 Drawing Sheets

(56) References Cited

U.S. PATENT DOCUMENTS

| | | | |
|---|---|---|---|
| 2005/0049747 A1* | 3/2005 | Willoughby | G07F 11/68 |
| | | | 700/232 |
| 2007/0185615 A1* | 8/2007 | Bossi | A61J 7/0084 |
| | | | 700/244 |
| 2012/0081225 A1 | 4/2012 | Waugh et al. | |
| 2013/0066463 A1* | 3/2013 | Luoma | G16H 20/13 |
| | | | 700/232 |
| 2013/0261794 A1* | 10/2013 | Fauci | G16H 20/13 |
| | | | 700/232 |
| 2015/0129602 A1 | 5/2015 | Medrano | |
| 2016/0371462 A1 | 12/2016 | Wallen et al. | |
| 2018/0243170 A1* | 8/2018 | Mahal | A61J 7/04 |
| 2018/0303719 A1* | 10/2018 | DeLury | A61J 1/03 |
| 2019/0133484 A1 | 5/2019 | Muuranto et al. | |
| 2019/0307647 A1* | 10/2019 | Greenspan | G16H 10/60 |
| 2020/0323738 A1 | 10/2020 | Bear et al. | |
| 2020/0375851 A1 | 12/2020 | Waugh et al. | |
| 2021/0225478 A1 | 7/2021 | Burrows et al. | |
| 2021/0343404 A1* | 11/2021 | Hunt | G16H 10/60 |

\* cited by examiner

MEDICATION ADHERENCE AND MONITORING SYSTEM AND METHOD

CROSS-REFERENCE TO RELATED APPLICATION(S)

This application claims priority to, and the benefit of, U.S. Provisional Application 63/546,625, filed Oct. 31, 2023, for all subject matter common to both applications. The disclosure of said provisional application is hereby incorporated by reference in its entirety.

FIELD OF THE INVENTION

The present invention relates to a medication adherence and monitoring system and method suitable for tracking compliance with a dosage schedule for a user. In particular, the present invention relates to a medication adherence system that alerts patients, caretakers, insurers, or authorized $3^{rd}$ parties at dose times, tracks the patient's manual extraction of the correct amount of medication, and provides immediate feedback regarding the extraction of medication to positively reinforce adherence to the dosage schedule, building a strong adherence habit.

BACKGROUND

In the field of medication management, it is often a challenge to ensure that patients adhere to their prescribed medication schedules. This is particularly true for patients with chronic conditions who may be required to take multiple medications at different times throughout the day. Mismanagement of medication can lead to serious health complications, including hospitalization or even death.

Packaging drugs for convenience in the form of a linear roll of pouches, blisters, or sachets has been in use in many European countries for many years. More recently in the US, a large mail-order pharmacy has coupled automated loading and inspection of sachets or packets holding multiple tablets and capsules with distribution of a linear spool of time labeled doses within a cardboard, passive, container (e.g., PillPack®). ExactCare® and White Cross Pharmacy Med-Pack® utilize similar packing technology.

While packaging multiple medications in sachets, packets, or pouches for dosing limits the need for the patient to deal with a plethora of bottles or vials containing single medications, the task of manually pulling a varying number of packets or pouches to achieve, for example, doses of greater than 15 pills at some time points, presents a daunting task for patients on complex regimens. This is especially the case for patients with the condition of Mild Cognitive Impairment, a diagnosis with increased prevalence among the elderly.

Therefore, there is a need for a system that can assist patients in managing their medication schedules effectively. However, some existing systems rely on manual input from the user to track dosages and what is being administered, which can be prone to error and may not be feasible for all users, particularly those with cognitive impairments or physical disabilities. Other systems involve interaction with complex graphic interfaces and computer controlled motoric advancing systems, which do not teach the patient to initiate a vigilant manual response, thereby precluding the powerful technology of Operant Conditioning to build a strong adherence habit and to teach the patient. These systems are complex and expensive to implement since the stream of pouches that must be advanced by mechanical systems is irregular, unpredictable, dependent on a patient's regimen of friable tablets, rigid capsules, or constantly evolving novel dose forms.

Furthermore, some of these systems may not provide real-time feedback to the user and/or healthcare providers about the user's adherence to their medication schedule, making it difficult to monitor and address non-adherence promptly.

SUMMARY

There is a need for a medication adherence and monitoring system that tracks compliance with a dosage schedule while providing feedback to the user regarding compliance with the dosage schedule. The present invention is directed toward further solutions to address this need, in addition to having other desirable characteristics. Specifically, the present invention is a very low-cost accessory to current pouching formats that is easy to load at home, enables the user to extract the medication in a familiar manner, tracks compliance, and provides real-time feedback regarding compliance to the user and/or designated caregivers. Family caregivers are highly invested in a loved one's adherence and their attention does not add the cost of contracted monitoring facilities. The device does not require the loading of cartridges or the involvement of specialized pharmacies.

The present invention provides a housing that mounts onto the containers or reservoirs currently used to store streams of pill packets, whether rolled, or accordion-folded, or other conventional configurations. This housing incorporates a medication adherence and monitoring system that utilizes a processor in conjunction with an optical scanner, to read scannable codes on the stream of pill packets both to configure the system and track extraction of the pill packets from the reservoir as they pass by the optical scanner and are manually pulled (extracted) from the reservoir through an opening in the housing. The housing further provides prompting and feedback for the extraction of the pill packets while monitoring compliance with the dosage schedule for the user.

In accordance with embodiments of the present invention, a medication adherence and monitoring system is provided. The system includes a housing, a gate, an optical scanning device, one or more indicator lights, a wireless transponder, and a processor. The housing is configured to mount on a medication reservoir that stores a stream of pill packets. The housing includes a top surface and an underside surface opposite the top surface, an opening passing through the top surface and the underside surface that is arranged and configured to allow passage of the stream of pill packets therethrough, and a flange extending from the housing along the underside surface and configured to engage with the medication reservoir to mount the housing on the medication reservoir. The gate is disposed across the opening of the housing and configured to support the stream of pill packets in the opening. The optical scanning device is disposed on the underside surface of the housing and configured to read a scannable code disposed on the stored stream of pill packets. The one or more indicator lights are disposed on the top surface of the housing and viewable from points outside of the medication adherence and monitoring system. The processor is in communication with the optical scanning device, one or more indicator lights, and a wireless transponder. The processor is configured to determine a medication dosage schedule for a user by processing data received from the optical scanning device scanning the scannable code disposed on the stream of pill packets;

display an indication to the user, using the indicator lights, the indication instructing the user to extract one or more pill packets of the stream of pill packets from the medication adherence and monitoring system based on the medication dosage schedule for the user; detect a status of extraction of one or more pill packets by processing data received from the optical scanning device scanning the scannable code disposed on the stream of pill packets before, during, or after extraction, wherein each pill packet has its own instance of the scannable code; provide feedback to the user, using the indicator lights, regarding the status of extraction of the one or more pill packets; and determine and record a status of compliance with the dosage schedule based on the status of extraction of the one or more pill packets of the stream of pill packets detected to have passed by the optical scanning device and been extracted through the opening of the housing.

In accordance with aspects of the present invention, the gate is configured to apply a friction force to a pill packet disposed in the gate to maintain the pill packet in position in the gate while still allowing a user to extract the pill packet. In other aspects, the gate comprises a brush grommet.

In accordance with aspects of the present invention, the scannable code comprises a QR code. In other aspects, the scannable code comprises a bar code.

In accordance with aspects of the present invention, the system further includes a roller attached to the flange configured to guide the stream of pill packets out of the medication reservoir and through the gate and opening in the top of the housing.

In accordance with aspects of the present invention, the processor is further configured to generate a message sent to a personal electronic device of the user. In some such aspects, generating a message involves sending a message, using the wireless transponder, to a remote server requesting that a message be sent to the personal electronic device of the user. In further such aspects, the remote server sends a message to the personal electronic device of the user. In other aspects, the processor is further configured to send the status of compliance to a remote server using the wireless transponder. In still other aspects, the processor is further configured to: generate a message sent to a caregiver for the user.

In accordance with aspects of the present invention, providing feedback comprises one or more of providing an indication that the user is to continue extracting the one or more pill packet, providing an indication that the user is near completion of extracting the one or more pill packets, and providing an indication that the user should stop extracting the one or more pill packets.

In accordance with aspects of the present invention, the one or more indicator lights comprise green, yellow, and red lights. In other aspects, the one or more indicator lights comprise a wireless connection status indicator.

In accordance with aspects of the present invention, the system further includes a travel mode.

In accordance with aspects of the present invention, providing feedback to the user, using the indicator lights, regarding the status of extraction of the one or more pill packets from the medication adherence and monitoring system provides operant conditioning for adhering to the dosage schedule.

In accordance with aspects of the present invention, determining a medication dosage schedule for a user further includes receiving an update about the medication dosage schedule from a remote server.

In accordance with aspects of the present invention, determining and recording a status of compliance with the dosage schedule further includes sending the status of compliance to a remote server. In some such aspects, the remote server may analyze the status of compliance and adjusts one or more of: the medication dosage schedule and the compliance status.

In accordance with embodiments of the present invention, a method of monitoring medication adherence is provided. The method involves providing a medication adherence and monitoring system as described herein; installing the medication adherence and monitoring system on a medication reservoir that stores a stream of pill packets; determining a medication dosage schedule for a user by processing data received from the optical scanning device scanning the scannable code disposed on the stream of pill packets; displaying an indication to the user, using the indicator lights, the indication instructing the user to extract one or more pill packets of the stream of pill packets from the medication adherence and monitoring system based on the medication dosage schedule for the user; detecting a status of extraction of one or more pill packets by processing data received from the optical scanning device scanning the scannable code disposed on the stream of pill packets before, during, or after extraction, wherein each pill packet has its own instance of the scannable code; providing feedback to the user, using the indicator lights, regarding the status of extraction of the one or more pill packets; and determining and recording a status of compliance with the dosage schedule based on the status of extraction of the one or more pill packets of the stream of pill packets detected to have passed by the optical scanning device and been extracted through the opening of the housing.

In accordance with aspects of the present invention, installing the medication adherence and monitoring system on a medication reservoir that stores a stream of pill packets involves inserting a first packet of the stream of pill packets into the opening on the underside surface of the housing and into the gate and mounting the housing on the medication reservoir so that the flanges engage the medication reservoir.

In accordance with aspects of the present invention, the method further involves generating a message sent to a personal electronic device of the user. In some such aspects, generating a message involves sending a message, using the wireless transponder, to a remote server requesting that a message be sent to the personal electronic device of the user. In still further such aspects, the remote server sends a message to the personal electronic device of the user.

In accordance with aspects of the present invention, providing feedback involves one or more of: providing an indication that the user is to continue extracting the one or more pill packets, providing an indication that the user is near completion of extracting the one or more pill packets, and providing an indication that the user should stop extracting the one or more pill packets.

In accordance with aspects of the present invention, the method further involves sending the status of compliance to a remote server using the wireless transponder.

In accordance with aspects of the present invention, the method further involves generating a message sent to a caregiver for the user.

In accordance with aspects of the present invention, determining a medication dosage schedule for a user further involves receiving an update about the medication dosage schedule from a remote server.

In accordance with aspects of the present invention, determining and recording a status of compliance with the dosage schedule further involves sending the status of compliance to a remote server. In some such aspects, the remote server may analyze the status of compliance and adjust one or more of: the medication dosage schedule and the compliance status.

By encouraging the user to extract their own medication and providing real-time feedback regarding compliance, the present invention makes use of the powerful behavior technology developed by B. F. Skinner, Operant Conditioning to form and maintain an adherence habit.

In classical conditioning (discovered by Ivan Pavlov), an unconditioned stimulus—e.g., food that elicits an autonomic response (salivation) is repeatedly paired with a neutral unconditioned stimulus, e.g., ringing of a bell, which then becomes a conditioned stimulus: i.e., the dog salivates when the bell is rung.

In contrast, B. F. Skinner discovered the Operant Conditioning paradigm for creating skeletal motor behavior or habits. Here, an organism must first "emit" a motor response, e.g., a pigeon pecks on a pad, which is then rapidly followed by a reinforcer, e.g., food for the hungry bird. The response becomes more frequent, i.e., the pigeon pecks repeatedly, which develops into the habit of pecking when it sees the key. The motoric initiated behavior of the organism, followed rapidly by the reinforcer, generates a habit or behavior that is stable (resistant to extinction).

In the present invention, a patient sees a signal (green light, called the Discriminative Stimulus indicating a reinforcer is available), pulls out medication pouches (getting haptic feedback from tactile resistance, visual signals from light icons)=emitted motor response. The patient's response is followed by rapid reinforcement (thumbs up icon blinking affirmation, technically a conditioned reinforcer that has been given positive value through learned associations. This increases the probability of the user pulling out the next pill packet(s) when the green light appears and creates an adherence habit.

In addition, the system can produce adherence and medication pull timing reports for any time interval. These reports can help a pharmacist or caregiver understand adherence patterns and make medication schedule adjustments to better serve the patient. In addition, machine learning and AI can be used to learn a patient's habits and automatically adjust dose timing alerts and caregiver escalation alerts. As an example, a patient may sleep later on weekends so the machine can adjust alerts. This would be similar to the Nest® thermostat learning over time when someone manually changes the thermostat setting and over time would make this new temperature setting part of the automatic schedule.

BRIEF DESCRIPTION OF THE FIGURES

These and other characteristics of the present invention will be more fully understood by reference to the following detailed description in conjunction with the attached drawings, in which.

DETAILED DESCRIPTION

Figure 1:
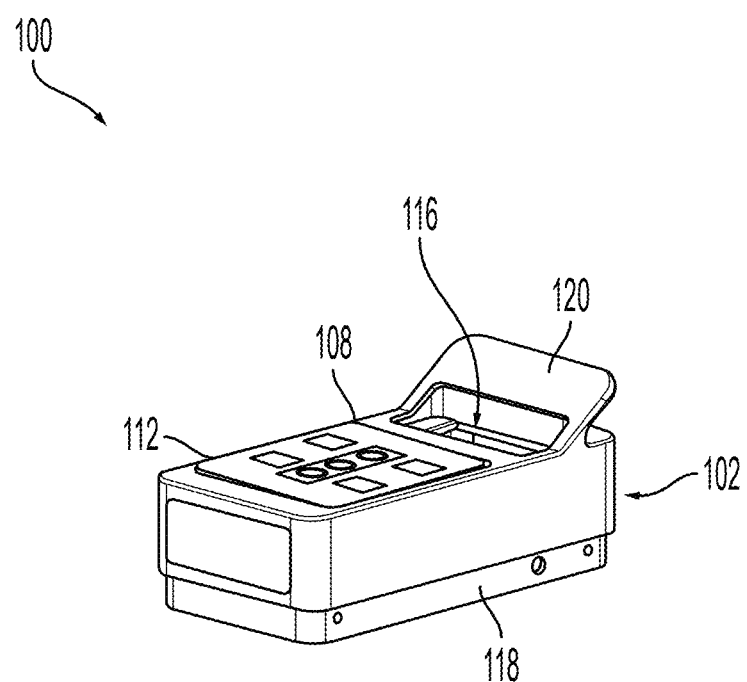
FIG. 1 is a perspective view of a medication adherence and monitoring system in accordance with embodiments of the present invention.

An illustrative embodiment of the present invention relates to a medication adherence and monitoring system for use with pill packet dosing. The system is configured to mount on a medication reservoir that stores a stream of pill packets. The system utilizes a processor in conjunction with an optical scanner, to read scannable codes on the stream of pill packets to configure the system and track extraction of the pill packets from the reservoir when they pass by the optical scanner as the pill packets are extracted from the reservoir through an opening in the housing. The system further provides prompting and feedback for the extraction of the pill packets while monitoring compliance with the dosage schedule for the user.

FIG. 1 through FIG. 10, wherein like parts are designated by like reference numerals throughout, illustrate an example embodiment or embodiments of a medication adherence and monitoring system, according to the present invention. Although the present invention will be described with reference to the example embodiment or embodiments illustrated in the figures, it should be understood that many alternative forms can embody the present invention. One of skill in the art will additionally appreciate different ways to alter the parameters of the embodiment(s) disclosed, such as the size, shape, or type of elements or materials, in a manner still in keeping with the spirit and scope of the present invention.

Figure 2:
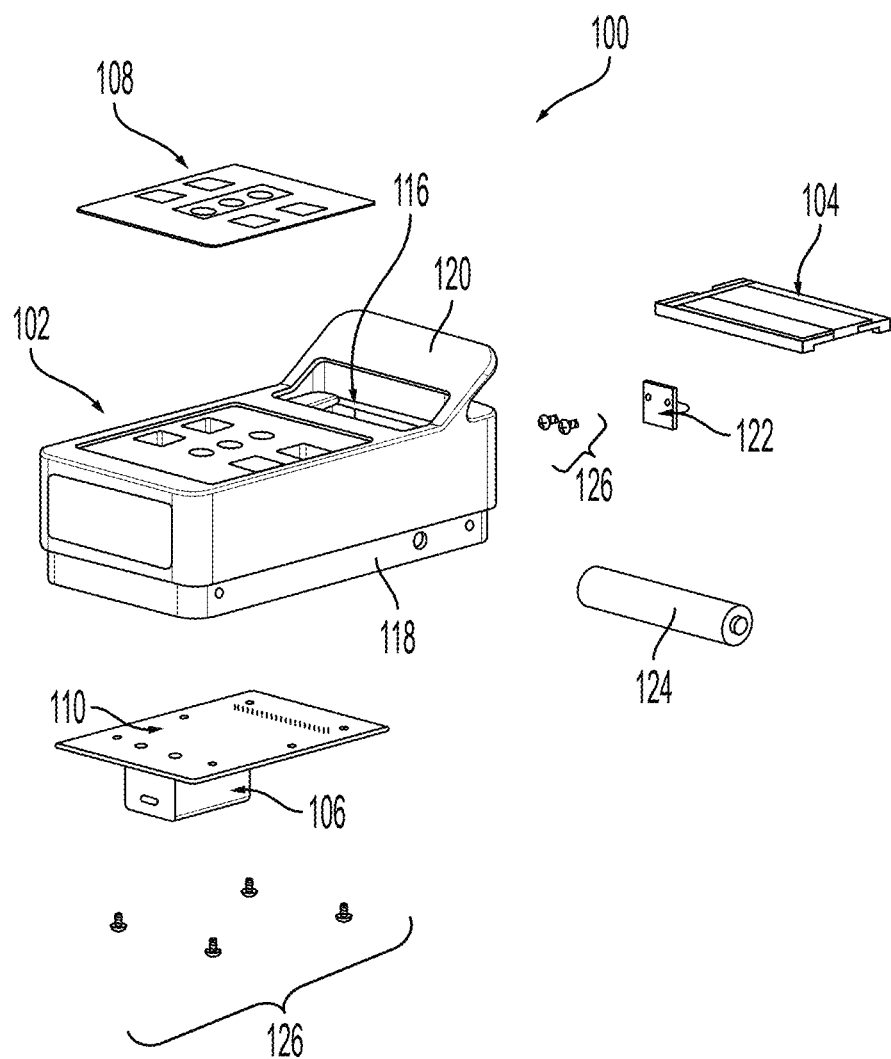
FIG. 2 is an exploded perspective view of a medication adherence and monitoring system in accordance with embodiments of the present invention.
Figure 3:
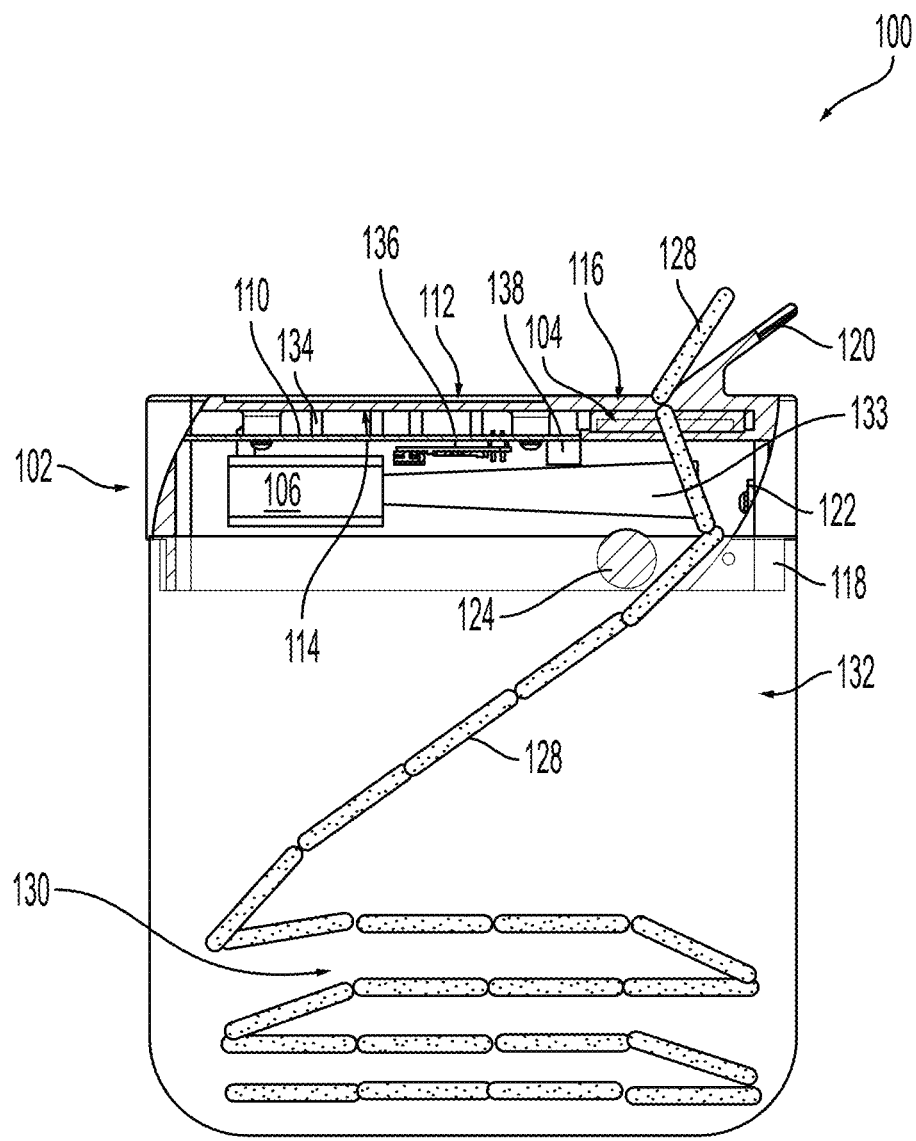
FIG. 3 is a transparent side view of a medication adherence and monitoring system in accordance with embodiments of the present invention.
Figure 4:
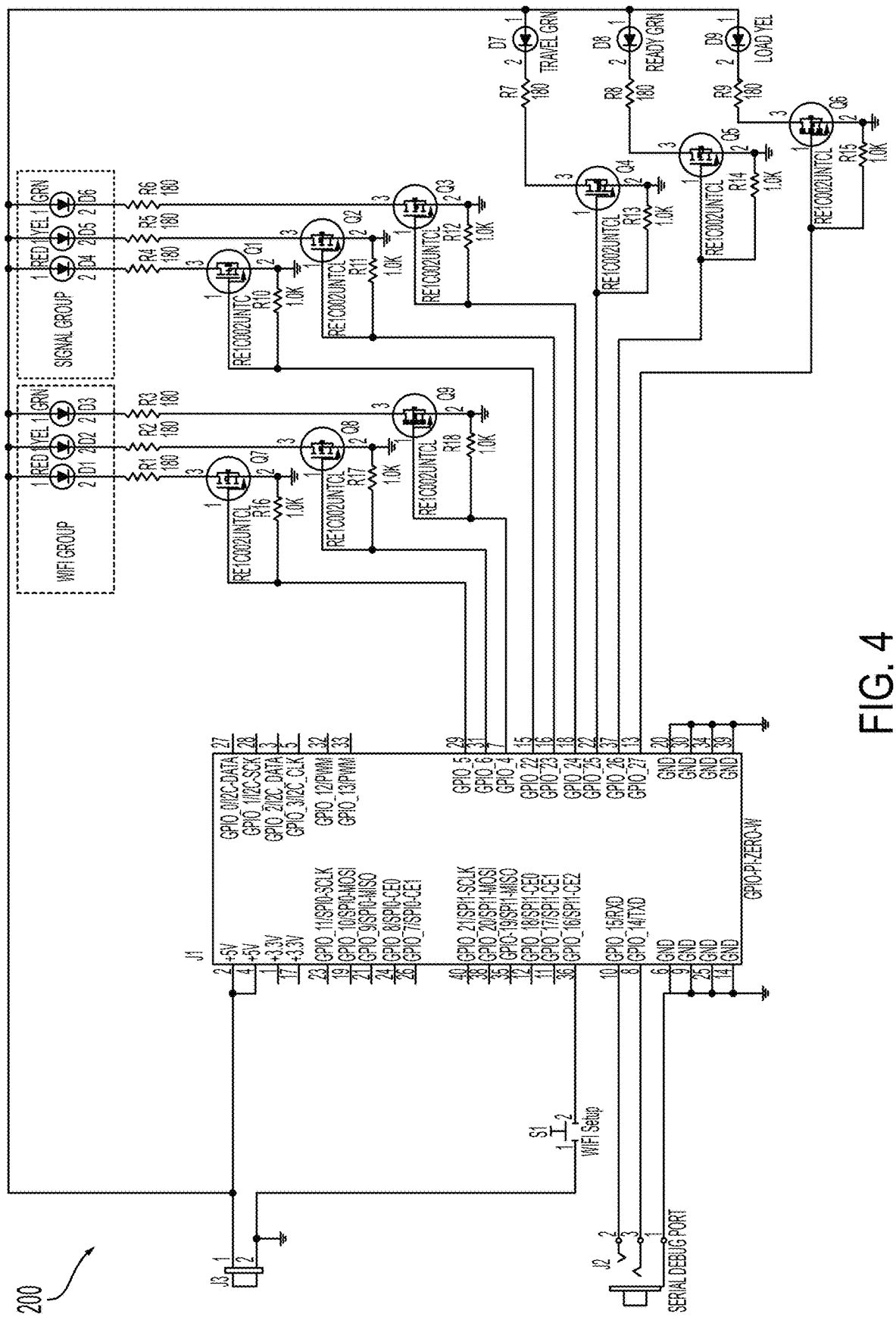
FIG. 4 is a circuit diagram for a controller board for a medication adherence and monitoring system in accordance with embodiments of the present invention.

As shown in FIG. 1 through FIG. 3, a medication adherence and monitoring system 100 is provided. The system includes a housing 102, a gate 104, an optical scanning device 106, one or more indicator lights 108, and a controller 110.

The housing 102 and one or more indicator lights 108 disposed on a top surface 112 of the housing 102 can be seen in FIG. 1. The housing 102 comprises the top surface 112, an underside surface 114 (see FIG. 2) opposite the top surface 112, an opening 116 passing through the top surface 112 and the underside surface 114, and a flange 118 extending from the housing 102 along the underside surface 114. In certain embodiments, the housing 102 further includes a support ledge 120 disposed in proximity to the opening 116.

The other components of the system can be seen in the exploded view of FIG. 2. Here, in addition to the housing 102 and one or more indicator lights 108 seen in FIG. 1, the gate 104, optical scanning device 106, and controller 110, can also be seen. In this embodiment, a power coupling 122, roller 124, and mounting hardware 126 are also shown.

The assembly of the housing 102, gate 104, optical scanning device 106, one or more indicator lights 108, and controller 110, as well as their relative positioning and interaction with pill packets 128 of the stream 130 of pill packets held in a medication reservoir 132 to which the housing 102 is mounted, can be seen FIG. 3. Here, on the housing 102, the underside surface 114 can be seen opposite the top surface 112 with the opening 116 passing through the top surface 112 and the underside surface 114 arranged and configured to allow the passage of the stream 130 of pill packets therethrough. The flange 118 extends from the housing 102 along the underside surface 114 and is configured to engage with the medication reservoir 132 to mount the housing 102 on the medication reservoir 132.

The housing 102 can be made from plastic, fiberglass, carbon fiber, metal, or any other suitable material. The housing 102 can be formed as one solid part or assembled from several smaller parts fastened together. The housing 102 is sized, dimensioned, and configured to act as a cover for a medication reservoir 132. Examples of such medication reservoirs 132 include the box that the stream 130 of pill packets is stored and shipped in for a dedicated medication as well reservoirs such as the PillPack® premium dispenser. In certain embodiments, the housing 102 may be attached to the medication reservoir 132 with a hinge or other mechanism wherein the system 100 can be moved to provide access to the medication reservoir 132 for refilling the reservoir with a stream 130 of pill packets. In still other embodiments, the housing may include latches or locking mechanisms to secure the housing 102 to the medication reservoir, preventing unauthorized access to the stream 130 of pill packets.

In certain embodiments, a roller 124 is attached to the flange 118. The roller 124 is configured to guide the stream 130 of pill packets out of the medication reservoir 132 and through the gate 104 and opening 116 in the top surface 112 of the housing 102.

In accordance with one example embodiment, the gate 104 is disposed across the opening 116 of housing 102 and is configured to support the stream 130 of pill packets in the opening 116. In certain embodiments, the gate 104 is configured to apply a friction force to a pill packet 128 disposed in the gate 104 to maintain the pill packet 128 in position in the gate 104 while still allowing a user to extract the pill packet 128. In some such embodiments, the gate 104 comprises a brush grommet. In other embodiments, the gate 104 comprises flaps made of silicon or another compliant material. Other possible configurations will be apparent to one skilled in the art given the benefit of this disclosure.

The optical scanning device 106 is disposed on the underside surface 114 of the housing 102 and configured to read a scannable code disposed on the stored stream 130 of pill packets. In this embodiment, the optical scanning device is mounted on the printed circuit board (PCB) 134 of the controller 110 which is turn mounted to the underside surface 114 of the housing 102. The optical scanning device 106 can be a camera, laser scanner, or any other device capable of scanning scannable codes such as bar codes or QR codes. The optical scanning device reads the scannable code of a pill packet 128 as it is held in place by the gate 104 as indicated by the field of view 133 for the optical scanning device 106.

Here, the controller 110 comprises a printed circuit board (PCB) 134 as well as a processor 136 and a wireless transponder 138. A schematic 200 for the circuit layout of the PCB 134 showing the communication channels between the processor 136, optical scanning device 106, and the wireless transponder 138 can be seen in FIG. 4. The processor 136 can be a Field Programmable Gate Array (FPGA), a controller, or any other type of processer capable of performing the functionality set forth herein. The wireless transponder 138 can be any suitable transponder capable of sending and receiving RF communications including, but not limited to, Wi-Fi, Bluetooth®, cellular, and near-field communications.

Figure 5:
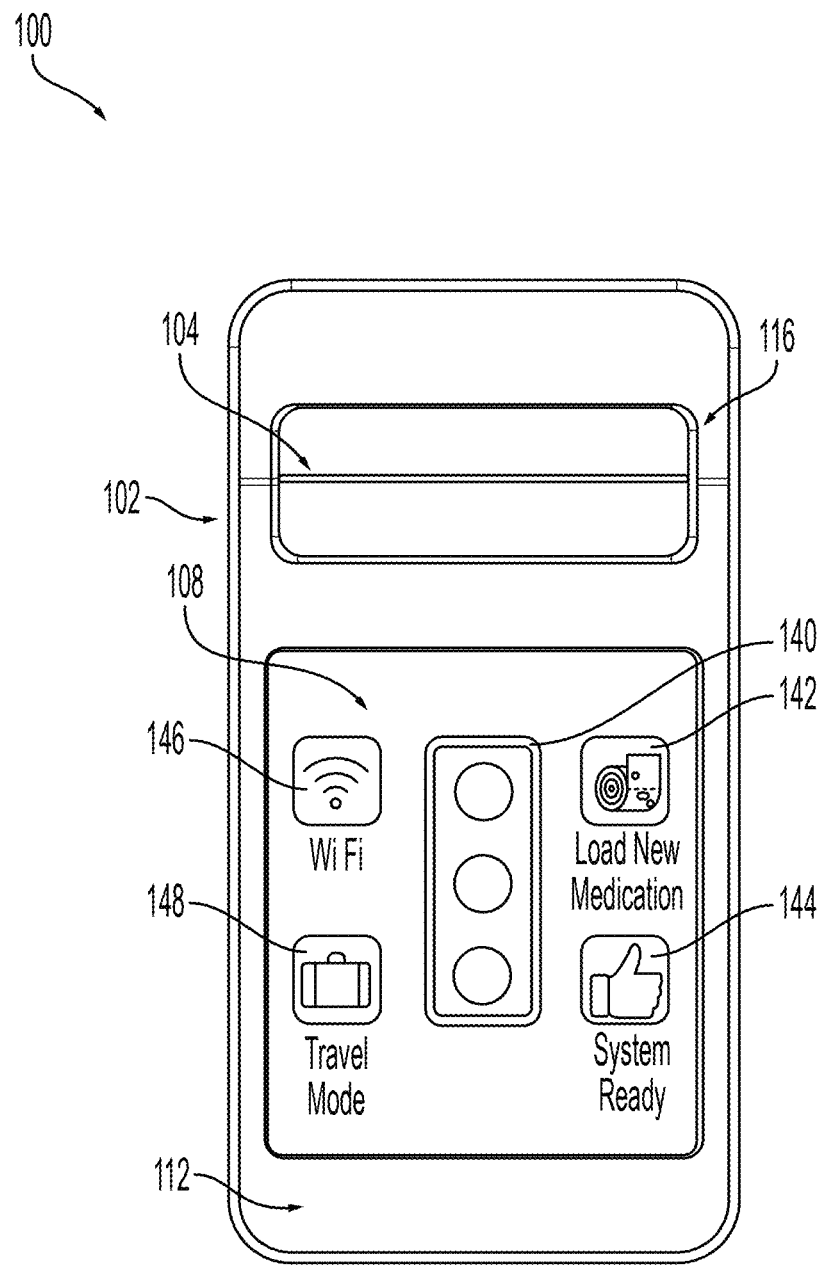
FIG. 5 is a top view of a medication adherence and monitoring system in accordance with embodiments of the present invention.

FIG. 5 depicts a top view of housing 102 of the system 100 showing the top surface 112, the opening 116, the gate 104, and the one or more indicator lights 108. Placing the one or more indicator lights 108 on the top surface allows them to be viewable from points outside the medication adherence and monitoring system 100. Here the one or more indicator lights 108 include an extraction status light 140, load new medication indicator light 142, system-ready indicator light 144, Wi-Fi status indicator light 146, and travel mode indicator 148. In this embodiment, the extraction status light 140 is configured to operate like a traffic light with a green light indicating to a user to extract pill packets 128, a yellow light indicating that the user should slow extraction of pill packets 128, and a red light indicating the user should stop extraction of pill packets 128. The load new medication indicator light 142 is configured to illuminate yellow indicating new medication needs to be loaded and stop illuminating when new medication has been loaded. The system-ready indicator light 144 is designed to illuminate green when new medication has successfully been loaded. The Wi-Fi status indicator light 146 illuminates green when a wireless communication for the system 100 has been established and illuminates red when the system 100 is disconnected. The Travel mode indicator 148 illuminated green when the system has been put into travel mode. In some embodiments, the travel mode indicator 148 may also act as a switch to toggle travel mode off and on. Other configurations and implementations will be apparent to one skilled in the art given the benefit of this disclosure.

Figure 6:
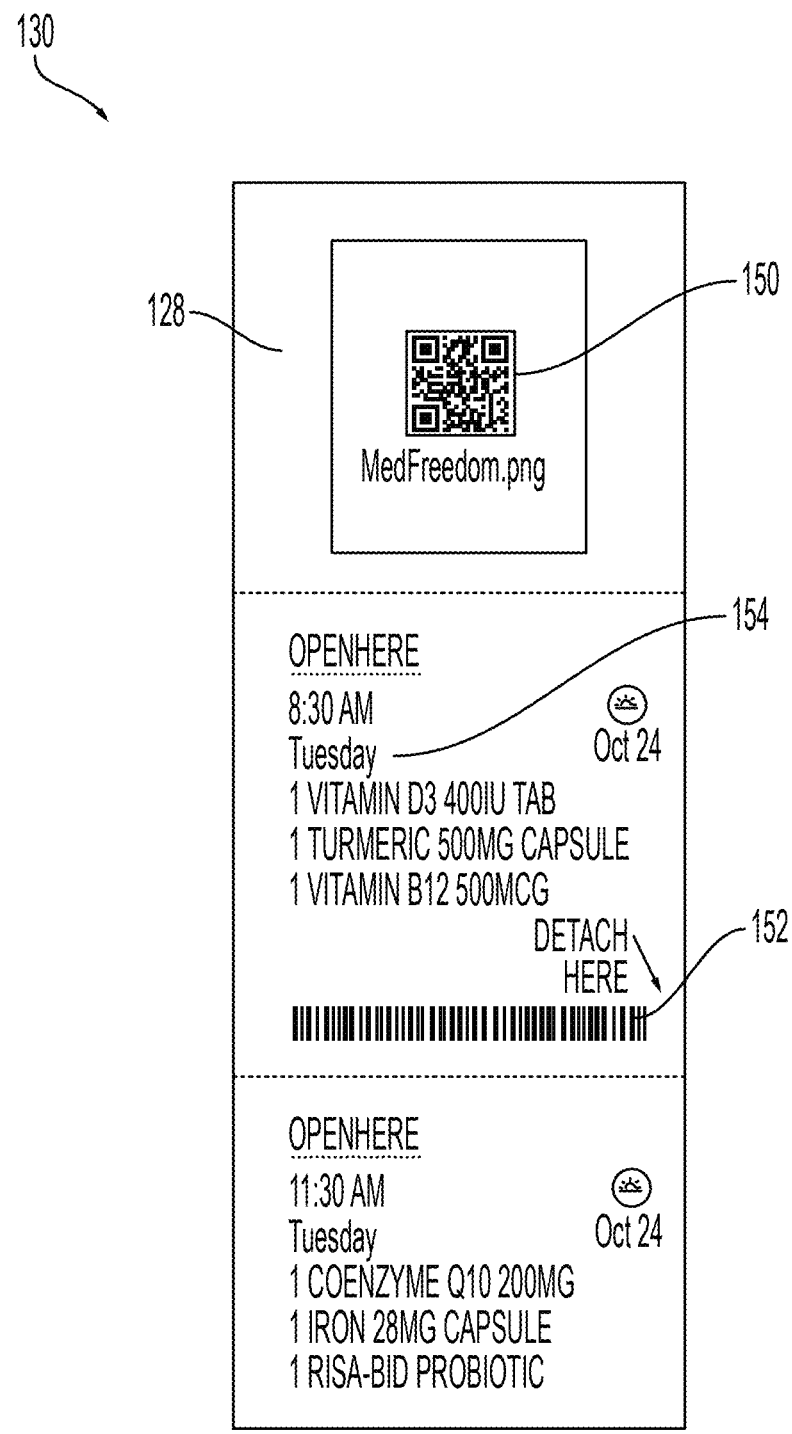
FIG. 6 depicts pill packets of a stream of pill packets used with a medication adherence and monitoring system in accordance with embodiments of the present invention.

FIG. 6 shows example pill packets 128 of the stream 130 of pill packets depicting various scannable codes disposed on the pill packets 128. Here the first pill packet 128 included in the stream 130 of pill packets has a QR code 150. This QR code 150 is read by the optical scanning device 106 and processed by the processor 136 to determine the medicine dosage schedule for the user. For example, the QR code 150 on the first pill packet 128 in the stream 130 of pill packets is used to determine the medical dosage schedule for the entire stream 130 of pill packets. Thus, with each new stream 130 of pill packets, a new medicine dosage schedule for that particular stream 130 of pill packets can be indicated by the QR code 150 disposed on the first pill packet 128 of the stream 130 of pill packets. Data provided by this QR code 150 can include the date for the prescription for the user, the total count of pill packets 128 in the stream 130 of pill packets, the start number for the pill packets 128 in the stream 130 of pill packets, the number of dosages in a day, the timing for dosages, and the number of pill packets 128 in a dosage, or the like.

The other pill packets 128 are shown to have a bar code 152 as well as dosage information 154. This bar code 152 indicated the number of the pill packet 128 in the stream 130 of pill packets 128. This bar code 152 is read by the optical scanning device 106 and processed by the processor 136 to determine that a pill packet 128 has been extracted. In this example, every pill packet 128 of the stream 130 of pill packets that is after the first pill packet 128 having the QR code 150 includes a bar code 152, where the number indicated by the bar code increments for each subsequent pill packet 128 in the stream 130 of pill packets.

As discussed previously, in some embodiments, the system can communicate directly with the Internet or other devices using Wi-Fi®, Bluetooth® Ethernet, and/or cellular connectivity, or other wireless communication protocol. An example of such connectivity can be seen in FIG. 7.

Figure 7:
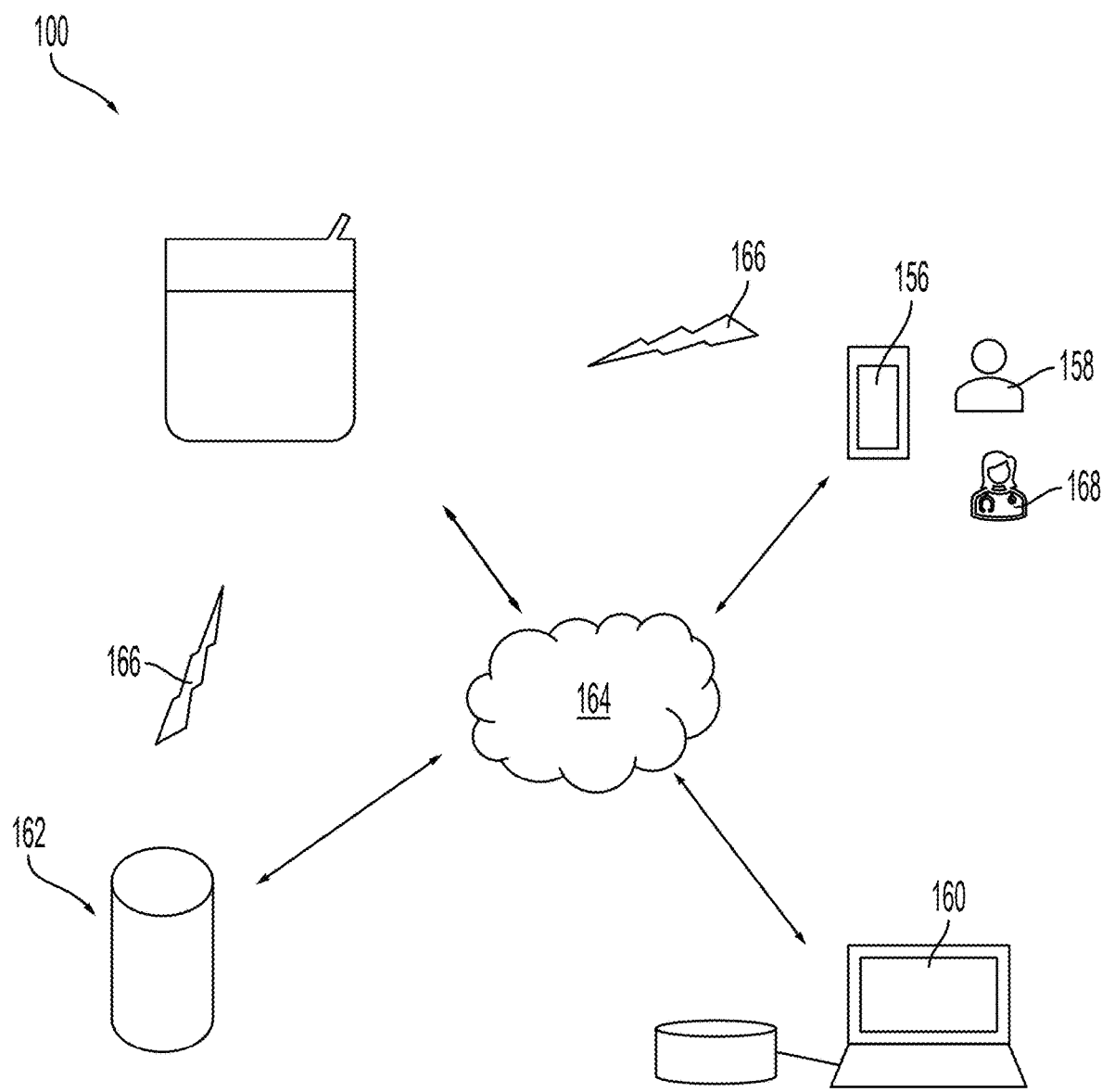
FIG. 7 depicts a communication network showing the connectivity of a medication adherence and monitoring system in accordance with embodiments of the present invention.

In the exemplary network of FIG. 7, the system 100 may be in communication with one or more devices such as a personal electronic or computing device 156 for a user, such as a smartphone, tablet, or personal computer; a remote monitoring system or server 160; and a smart device 162 such as a smart speaker, such as Amazon Echo™ or Google Home™. The communication may be over the internet 164 or through direct device-to-device communication 166 such as radio, Bluetooth®, or cellular communication, or the like. The personal electronic or computing device 156 allows a user, either a patient 158 or caregiver 168, to control and configure the operation of the system 100. Similarly, the system 100 can be controlled by the remote monitoring system or server 160 allowing hospitals, nursing homes, or other care facilities fleet management of the system 100. The remote monitoring system or server 160 may also be used by the system 100 to confirm medications and dosages provided by the pill packets 128 and receive updates on dosage schedule.

In some embodiments, compliance data are stored internally and retrieved manually, e.g., by copying files to a USB flash drive. This allows monitoring even when Internet access is not available or desired.

Figure 8:
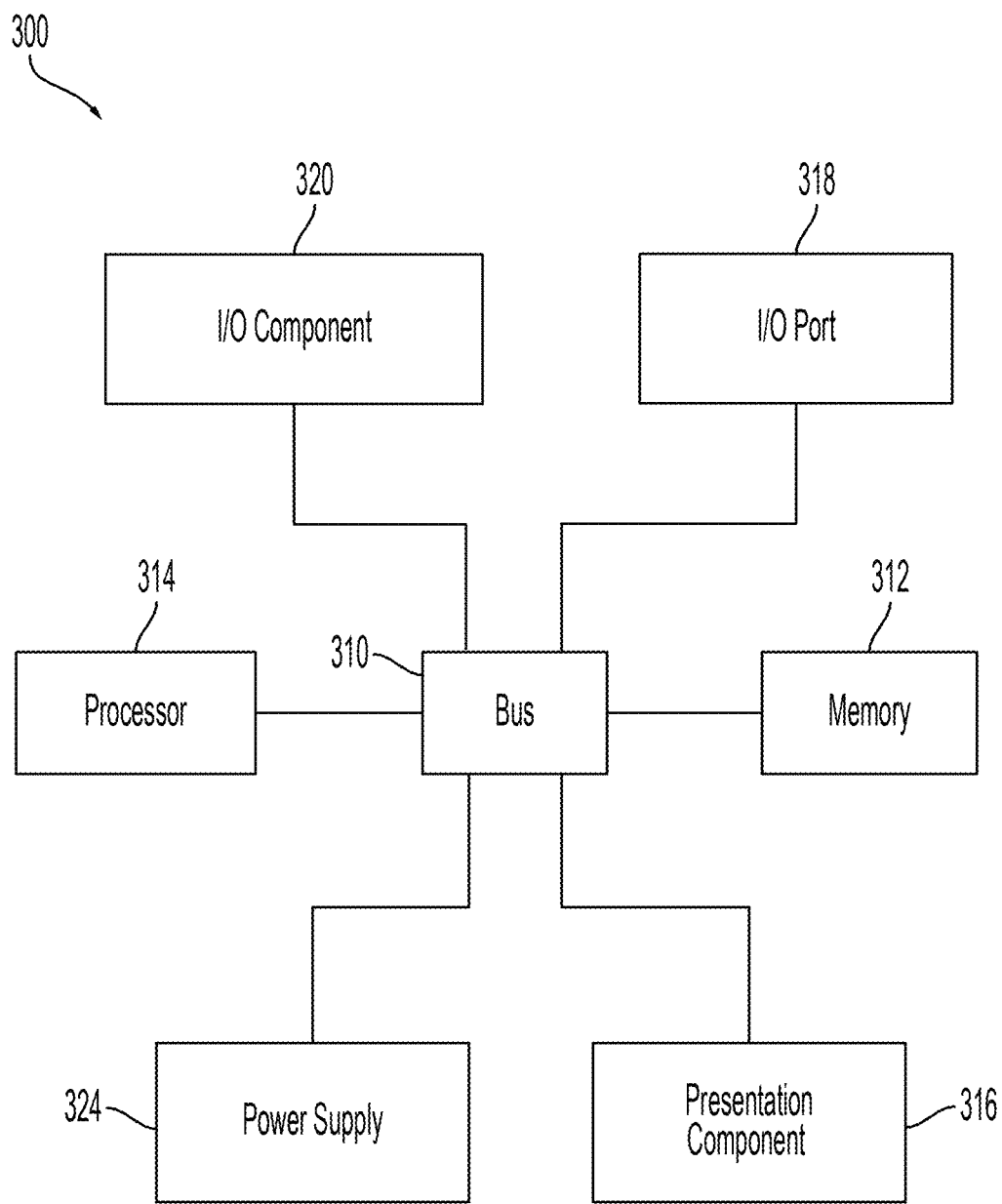
FIG. 8 is a diagrammatic illustration of a computing device and related hardware for use in the implementation of the present invention.

FIG. 8 depicts an example electronic, computer, or computing device 300 that can be used to implement one or more aspects of the present invention, including control of the system 100 or personal electronic or computing device 156, remote monitoring system or server 160, or smart device 162. The functionality and hardware of such computing device 300 may be implemented in any of the electronic hardware systems or subsystems described herein as involving or using a "computer" or "computing device" or the like, or related hardware for providing all or part of the described functionality, provided as a separate device or integrated into a system or subsystem described herein, as would be appreciated and understood by those of skill in the art. The terms "computer", "computing device", and the like utilized herein are intended to mean a processor at its most basic form, on up to more complex computing systems, including servers and cloud-based systems, in accordance with conventional meanings of such terms. However, for the purpose of completeness, example components and related accessories that are intended to be encompassed by the use of the terms "computer", "computing device", "processor", and the like will be provided below in example nonlimiting form.

The computing device 300 is merely an illustrative example of a suitable computing environment and in no way limits the scope of the present invention. An "electronic device", "remote device," or "personal electronic device" as represented in figures and description herein, can include a "workstation," a "server," a "laptop," a "desktop," a "handheld device," a "mobile device," a "tablet computer," a "processor," or other computing devices, as would be understood by those of skill in the art. Given that the computing device 300 is depicted for illustrative purposes, embodiments of the present invention may utilize any number of computing devices 300 in any number of different ways to implement a single embodiment of the present invention. Accordingly, embodiments of the present invention are not limited to a single computing device 300, as would be appreciated by one with skill in the art, nor are they limited to a single type of implementation or configuration of the example computing device 300.

The computing device 300 can include a bus 310 that can be coupled to one or more of the following illustrative components, directly or indirectly: a memory 312, one or more processors 314, one or more presentation components 316, input/output ports 318, input/output components 320, and a power supply 324. One of skill in the art will appreciate that the bus 310 can include one or more busses, such as an address bus, a data bus, or any combination thereof. One of skill in the art additionally will appreciate that, depending on the intended applications and uses of a particular embodiment, multiple of these components can be implemented by a single device. Similarly, in some instances, a single component can be implemented by multiple devices. As such, the figures herein are merely illustrative of an exemplary computing device 300 that can be used to implement one or more embodiments of the present invention, and in no way limits the invention.

The computing device 300 can include or interact with a variety of computer-readable media. For example, computer-readable media can include Random Access Memory (RAM); Read Only Memory (ROM); Electronically Erasable Programmable Read Only Memory (EEPROM); flash memory or other memory technologies; CDROM, digital versatile disks (DVD) or other optical or holographic media; magnetic cassettes, magnetic tape, magnetic disk storage or other magnetic storage devices that can be used to encode information and can be accessed by the computing device 300.

The memory 312 can include computer-storage media in the form of volatile and/or nonvolatile memory. The memory 312 may be removable, non-removable, or any combination thereof. Exemplary hardware devices are devices such as hard drives, solid-state memory, optical-disc drives, and the like. The computing device 300 can include one or more processors that read data from components such as the memory 312, the various I/O components 320, etc. Presentation component(s) 316 present data indications to a user or other device. Exemplary presentation components include a display device, speaker, printing component, vibrating component, etc.

The I/O ports 318 can enable the computing or electronic device 300 to be logically coupled to other devices, such as I/O components 320. Some of the I/O components 320 can be built into the computing device 300. Examples of such I/O components 320 include a sensor (including but not limited to: weight sensor, infrared sensor, camera, chemical sensor, microphone, or the like), keypad, touchpad, joystick, recording or storage device, game pad, satellite dish, scanner, printer, wireless device, networking device, and the like, as appropriate.

To set up the system 100, the user plugs in the system 100 using the power coupling 122, here a USB plug, and powers on the system. The user may then set up the wireless connectivity for the system. In some embodiments, this is done by connecting a personal electronic device 156 to the USB plug. In other embodiments, the user may use an application on a personal electronic device 156 to connect directly to the system 100 over Bluetooth using the wireless transponder 138. Once set up, the system 100 is then ready to begin its regular operation.

Figure 9:
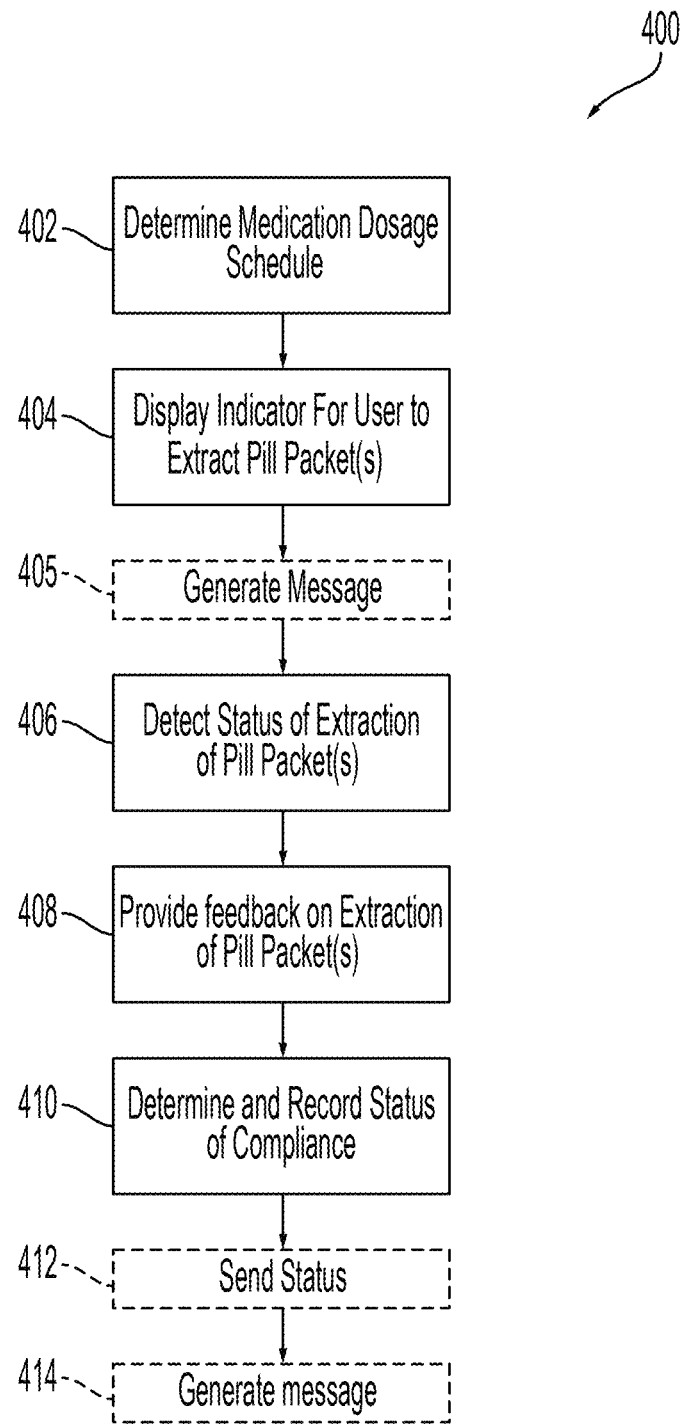
FIG. 9 is an example flow diagram for the operation of a medication adherence and monitoring system in accordance with embodiments of the present invention.

FIG. 9 depicts an example flow diagram 400 depicting the functionality performed by the processor 136 in conjunction with the optical scanning device 106, one or more indicator lights 108, and the wireless transponder 138. The processor 136 executes code which in turn configures the processor 136 to: determine a medication dosage schedule for a user (Step 402), display an indicator to the user instructing the user to extract one or more pill packets 128 (Step 404), detect status of extraction of the one or more pill packets 128 (Step 406), provide feedback regarding the status of extraction (Step 408)

The medication dosage schedule is determined (Step 402) by processing data received from the optical scanning device 106 scanning the scannable code disposed on the stream 130 of pill packets. Here the scannable code is the QR code 150 as seen and described in reference to FIG. 6. The medication dosage schedule includes the times for extraction of pill packets 128 as well as the number of pill packets 128 to be extracted at each time. In certain embodiments, updates to the medication dosage schedule can be received from the remote monitoring system or server 160.

The one or more indicator lights 108 are used to display an indication to the user (Step 404) instructing the user to extract one or more pill packets 128 of the stream 130 of pill packets from the medication adherence and monitoring system 100 based on the medication dosage schedule for the user. As discussed in reference to FIG. 5 this can include having extraction status light 140 illuminate with a green light indicating to a user to extract pill packets 128.

In certain embodiments, the system 100 may further generate a message to be sent to a user's personal electronic device 156 (Step 405). This message can be a text or email instructing the user to extract pill packets 128 from the system 100. In some embodiments, a message is generated and sent by the system 100 using the wireless transponder 138. In other embodiments, generating a message involves sending a message, using the wireless transponder 138, to a remote server 160 requesting that a message be sent to the personal electronic device 156 of the user. The remote server 160 can then send a message to the personal electronic device 156 of the user. In certain embodiments, the remote server may send messages based on changes to the dosage schedule, change of medication, or analysis of historical compliance data.

The status of extraction of one or more pill packets is detected (Step 406) by processing data received from the optical scanning device 106 scanning the scannable code disposed on the stream 130 of pill packets before, during, or after extraction, wherein each pill packet 128 has its own instance of the scannable code. Here the scannable code is the bar code 152 as seen and described in reference to FIG. 6.

Feedback regarding the status of extraction of the one or more pill packets is provided to the user (Step 408), using the one or more indicator lights 108. As discussed in reference to FIG. 5 this can include having extraction status light 140 illuminate with a green light indicating to a user to continue to extract pill packets 128, illuminating with a yellow light indicating that the user should slow extraction of pill packets 128 as they are nearing the end of extraction, and illuminate a red light indicating the user should stop extraction of pill packets 128 as extraction is complete.

The determination and recording of the status of compliance with the dosage schedule (Step 410) is based on the status of extraction of the one or more pill packets 128 of the stream 130 of pill packets detected to have passed by the optical scanning device 106 and been extracted through the opening 116 of the housing 102. The recorded status can then be reviewed by the user. In certain embodiments, this can be done directly by accessing the system 100 via with wireless transponder or USB port. In addition to specified times for dosage, the system 100 may also be configured to track compliance based intervals of time such as morning, mid-day, afternoon, evening.

In some embodiments, the processor 136 is further configured to transmit or otherwise send the status of compliance for the user to a remote server 160 (Step 412) where it can be stored and analyzed. In certain embodiments, this allows the system 100 to be further customized to a particular user. For example, week-day vs weekend behavior can be captured and the dosage schedule adjusted accordingly. In some such embodiments, remote server 160 can use machine learning or other artificial intelligence to track compliance and adjust the system's 100 monitoring and notifications accordingly.

In certain embodiments, a message can be generated to be sent to a caregiver 168 (Step 414) to notify the caregiver 168 of the status of compliance of the user. This message can be a text or email. In some embodiments, the message is generated and sent by the system 100 using the wireless transponder 138. In other embodiments, generating a message involves sending a message, using the wireless transponder 138, to a remote server 160 requesting that a message be sent to the caregiver 168. The remote server 160 can then send a message to the caregiver 168.

In one embodiment, connectivity to the remote server 160 allows for more rapid response to a change in the user's medication or dosage schedule. Updates or changes in dosage schedule and/or changes to the medication can be sent to the system 100 so that when a user extracts pill packets 128 that do not comply with received updates or changes, the system 100 provides an indication to stop with the extraction. In one example, if a medication is discontinued, the user and/or caregiver could receive a notification of the discontinued medicine which could include a picture of the medicine and/or a listing of pouches that contain the medicine while the system 100 could receive an update so that when a pill packet 128 of discontinued medication extracted, the system 100 provides a notification to the user and or caregiver, not to use the medication. In another example, if an additional medication, for which there is no pill packet 128 available such as a liquid, spray, or injection, is added to the dosage schedule, the user could be provided with a notification to take the additional medication in conjunction with their medication extracted through the system 100 while the system 100 could receive an update so that when a pill packet 128 medication extracted, the system 100 provides a notification to the user and or caregiver, take the additional medication as well.

Figure 10:
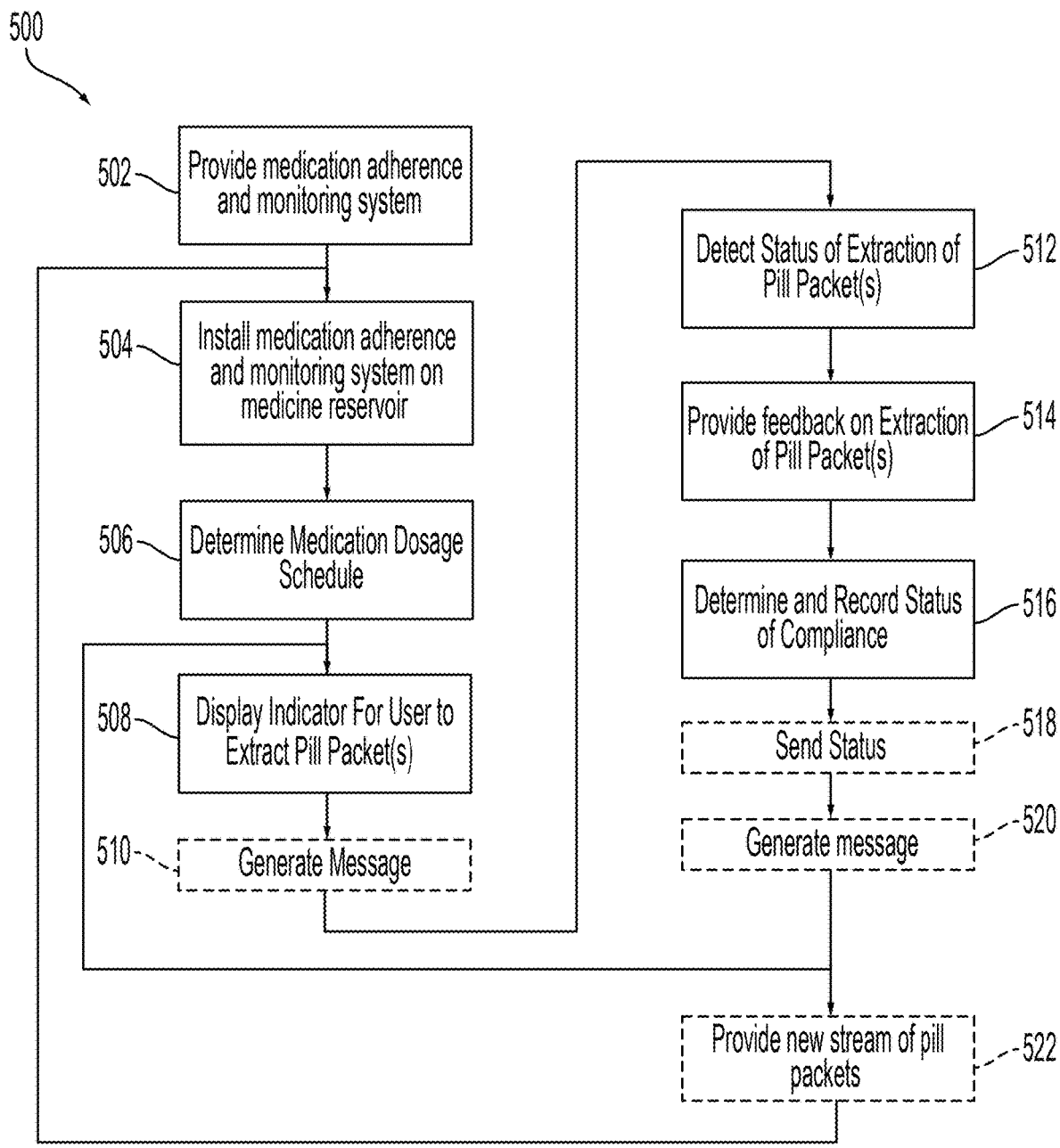
FIG. 10 is an example flow diagram for the use of a medication adherence and monitoring system in accordance with embodiments of the present invention.

FIG. 10 depicts an example flow diagram 400 depicting a method 500 for using the medication adherence and monitoring system 100 described herein. The method 500 begins with a medication adherence and monitoring system 100 being provided to the user (Step 502). The provided medication adherence and monitoring system 100 can then be installed on the medication reservoir 132 holding or storing a stream 130 of pill packets (Step 504).

In certain embodiments, installing the medication adherence and monitoring system 100 on the medication reservoir 132 comprises inserting a first packet 128 of the stream 130 of pill packets into the opening 116 on the underside surface 114 of the housing 102 and into the gate 104 and mounting the housing 102 on the medication reservoir 132 so that the flanges 118 engage the medication reservoir 132. Once the system 100 is mounted on the reservoir 132 (Step 504), the medication dosage schedule can be determined (Step 506). This can be performed in the manner set forth above in regards to Step 402 of FIG. 9. Next an indication for the user to extract one or more a pill packets 128 (Step 508). This can be performed in the manner set forth above in regards to Step 404 of FIG. 9.

In certain embodiments, the method 500 may further include generating a message to be sent to a user's personal electronic device 156 (Step 510). This message can be a text or email instructing the user to extract pill packets 128 from the system 100. In some embodiments, a message is generated and sent by the system 100 using the wireless transponder 138. In other embodiments, generating a message involves sending a message, using the wireless transponder 138, to a remote server 160 requesting that a message be sent to the personal electronic device 156 of the user. The remote server 160 can then send a message to the personal electronic device 156 of the user. In certain embodiments, the remote server may send messages based on a changes to the dosage schedule, change of medication, or analysis of historical compliance data.

The status of extraction of one or more pill packets can be detected (Step 512) by processing data received from the optical scanning device 106 scanning the scannable code disposed on the stream 130 of pill packets before, during, or after extraction, wherein each pill packet 128 has its own instance of the scannable code. This can be performed in the manner set forth above in regards to Step 406 of FIG. 9

Feedback regarding the status of extraction of the one or more pill packets can then be provided to the user (Step 514), using the one or more indicator lights 108. This can be performed in the manner set forth above in regards to Step 408 of FIG. 9

Similarly, the determination and recording of the status of compliance with the dosage schedule (Step 516) can be performed in the manner set forth above in regards to Step 410 of FIG. 9

In some embodiments, the method 500 further involves transmitting or otherwise sending the status of compliance for the user to a remote server 160 (Step 518) where it can be stored and analyzed. In certain embodiments, this allows the system 100 to be further customized to a particular user. For example, week-day vs weekend behavior can be captured and the dosage schedule adjusted accordingly. In some such embodiments, remote server 160 can use machine learning or other artificial intelligence to track compliance and adjust the system's 100 monitoring and notifications accordingly.

In certain embodiments, a message can be generated to be sent to a caregiver 168 (Step 520) to notify the caregiver 168 of the status of compliance of the user. This message can be a text or email. In some embodiments, the message is generated and sent by the system 100 using the wireless transponder 138. In other embodiments, generating a message involves sending a message, using the wireless transponder 138, to a remote server 160 requesting that a message be sent to the caregiver 168. The remote server 160 can then send a message to the caregiver 168.

After every dosage extraction the process may restart at step 508 for the extraction of the next dosage. When the last pill packet 128 of the stream 130 of pill packets is extracted, a new medicine reservoir 132 holding a stream 130 of pill packet or a new stream 130 of pill packets to be stored in the existing reservoir can be provided (step 522) and the process can restart at step 504.

As set forth previously, connectivity to the remote server 160 allows for more rapid response to a change in the user's medication or dosage schedule. Updates or changes in dosage schedule and/or changes to the medication can be sent to the system 100 so that when a user extracts pill packets 128 that do not comply with received updates or changes, the system 100 provides an indication to stop with the extraction. In one example, if a medication is discontinued, the user and/or caregiver could receive a notification of the discontinued medicine which could include a picture of the medicine and/or a listing of pouches that contain the medicine while the system 100 could receive an update so that when a pill packet 128 of a discontinued medication is extracted, the system 100 provides a notification to the user and or caregiver, not to use the medication. In another example, if an additional medication, for which there is no pill packet 128 available such as a liquid, spray, or injection, is added to the dosage schedule, the user can be provided with a notification to take the additional medication in conjunction with their medication extracted through the system 100, while the system 100 can receive an update so that when a pill packet 128 medication extracted, the system 100 provides a notification to the user and or caregiver, take the additional medication as well.

In some embodiments, the system 100 further includes a travel/vacation mode. When the system is placed in travel/vacation mode, the daily tracking for extraction is suspended allowing the user to extract as many pill packets 128 as necessary to provide dosages during the period travel/vacation mode is activated without requiring that the entire supply of pill packets or the medication reservoir 132 accompany the user who is traveling or on vacation. Daily tracking is then resumed at the time travel/vacation mode is terminated.

By encouraging the user to extract their own medication and providing real-time feedback regarding compliance, using the indicator lights, regarding the status of extraction of the one or more pill packets from the medication adherence and monitoring system provides operant conditioning to reinforce adherence with the dosage schedule for the user. In terms of behavioral psychology first established by B. F. Skinner, the patient's removal of pouches following a reminding signal constitutes Operant Behavior, subject to increased frequency by a reinforcer. This distinguishes the device from motorized dispensers which do not rely on the patient emitting a response.

Some additional advantages of the present invention include but are not limited to the following, The inventive device is a low-cost accessory that mounts on a conventional container for currently distributed pouches. There is no requirement for a more expensive display screen with a graphical user interface, a proprietary cartridge, a motor for the advancement of a pill packet, a drive train, or the like. Because of the design of the inventive device, there is no routine maintenance required to keep the device in operating condition other than periodic battery replacement. The device is compatible with current conventional pill pouching products. The operation directs manual removal of pouches via a simple pulling action, so requires no new learning (crystallized intelligence preserved even in early dementia). Furthermore, the inventive device does not block a patient's access to medications (easily removed from the packet reservoir to access the pill packets if necessary).

As utilized herein, the terms "comprises" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about", "generally", and "approximately" are intended to cover variations that may exist in the upper and lower limits of the ranges of subjective or objective values, such as variations in properties, parameters, sizes, and dimensions. In one non-limiting example, the terms "about", "generally", and "approximately" mean at, or plus 10 percent or less, or minus 10 percent or less. In one non-limiting example, the terms "about", "generally", and "approximately" mean sufficiently close to be deemed by one of skill in the art in the relevant field to be included. As utilized herein, the term "substantially" refers to the complete or nearly complete extent or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification, embodiments have been described in a way that enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A medication adherence and monitoring system comprising:
    a housing configured to mount on a medication reservoir that stores a stream of pill packets, the housing comprising:
        a top surface and an underside surface opposite the top surface;
        an opening passing through the top surface and the underside surface that is arranged and configured to allow passage of the stream of pill packets therethrough; and
        a flange extending from the housing along the underside surface and configured to engage with the medication reservoir to mount the housing on the medication reservoir;
    a gate disposed across the opening of the housing and configured to support the stream of pill packets in the opening;
    an optical scanning device disposed on the underside surface of the housing and configured to read a scannable code disposed on the stored stream of pill packets;
    one or more indicator lights disposed on the top surface of the housing and viewable from points outside of the medication adherence and monitoring system;
    a wireless transponder; and
    a processor in communication with the optical scanning device, one or more indicator lights, and wireless transponder, the processor configured to:
        determine a medication dosage schedule for a user by processing data received from the optical scanning device scanning the scannable code disposed on the stream of pill packets;
        display an indication to the user, using the indicator lights, the indication instructing the user to extract one or more pill packets of the stream of pill packets from the medication adherence and monitoring system based on the medication dosage schedule for the user;
        detect a status of extraction of one or more pill packets by processing data received from the optical scanning device scanning the scannable code disposed on the stream of pill packets before, during, or after extraction, wherein each pill packet has its own instance of the scannable code;
        provide feedback to the user, using the indicator lights, regarding the status of extraction of the one or more pill packets; and
        determine and record a status of compliance with the dosage schedule based on the status of extraction of the one or more pill packets of the stream of pill packets detected to have passed by the optical scanning device and been extracted through the opening of the housing.

2. The system of claim 1, wherein the gate is configured to apply a friction force to a pill packet disposed in the gate to maintain the pill packet in position in the gate while still allowing a user to extract the pill packet.

3. The system of claim 1, wherein the gate comprises a brush grommet.

4. The system of claim 1, wherein the scannable code comprises a QR code.

5. The system of claim 1, wherein the scannable code comprises a bar code.

6. The system of claim 1, further comprising a roller attached to the flange configured to guide the stream of pill packets out of the medication reservoir and through the gate and opening in the top of the housing.

7. The system of claim 1, wherein the processor is further configured to:
    generate a message sent to a personal electronic device of the user.

8. The system of claim 7, where generating a message comprises:
    sending a message, using the wireless transponder, to a remote server requesting that a message be sent to the personal electronic device of the user.

9. The system of claim 8, wherein the remote server sends a message to the personal electronic device of the user.

10. The system of claim 1, wherein providing feedback comprises one or more of:
providing an indication that the user is to continue extracting the one or more pill packet;
providing an indication that the user is near completion of extracting the one or more pill packets; and
providing an indication that the user should stop extracting the one or more pill packets.

11. The system of claim 1, wherein the one or more indicator lights comprise green, yellow, and red lights.

12. The system of claim 1, wherein the one or more indicator lights comprise a wireless connection status indicator.

13. The system of claim 1, wherein the processor is further configured to:
send the status of compliance to a remote server using the wireless transponder.

14. The system of claim 1, wherein the processor is further configured to:
generate a message sent to a caregiver for the user.

15. The system of claim 1, further comprising a travel mode.

16. The system of claim 1, where providing feedback to the user, using the indicator lights, regarding the status of extraction of the one or more pill packets from the medication adherence and monitoring system provides operant conditioning for adhering to the dosage schedule.

17. The system of claim 1, wherein determining a medication dosage schedule for a user further comprises:
receiving an update about the medication dosage schedule from a remote server.

18. The system of claim 1, wherein determining and recording a status of compliance with the dosage schedule further comprises:
sending the status of compliance to a remote server.

19. The system of claim 18, wherein the remote server analyzes the status of compliance and adjusts one or more of:
the medication dosage schedule; and
the compliance status.

20. A method of monitoring medication adherence, the method comprising:
providing a medication adherence and monitoring system comprising:
a housing configured to mount on a medication reservoir that stores a stream of pill packets, the housing comprising:
a top surface and an underside surface opposite the top surface;
an opening passing through the top surface and the underside surface that is arranged and configured to allow passage of the stream of pill packets therethrough; and
a flange extending from the housing along the underside surface and configured to engage with the medication reservoir to mount the housing on the medication reservoir;
a gate disposed across the opening of the housing and configured to support the stream of pill packets in the opening;
an optical scanning device disposed on the underside surface of the housing and configured to read a scannable code disposed on the stored stream of pill packets;
one or more indicator lights disposed on the top surface of the housing and viewable from points outside of the medication adherence and monitoring system;
a wireless transponder; and
a processor in communication with the optical scanning device, one or more indicator lights, and wireless transponder, the processor configured to:
determine a medication dosage schedule for a user by processing data received from the optical scanning device scanning the scannable code disposed on the stream of pill packets;
display an indication to the user, using the indicator lights, the indication instructing the user to extract one or more pill packets of the stream of pill packets from the medication adherence and monitoring system based on the medication dosage schedule for the user;
detect a status of extraction of one or more pill packets by processing data received from the optical scanning device scanning the scannable code disposed on the stream of pill packets before, during, or after extraction, wherein each pill packet has its own instance of the scannable code;
provide feedback to the user, using the indicator lights, regarding the status of extraction of the one or more pill packets; and
determine and record a status of compliance with the dosage schedule based on the status of extraction of the one or more pill packets of the stream of pill packets detected to have passed by the optical scanning device and been extracted through the opening of the housing;
installing the medication adherence and monitoring system on a medication reservoir that stores a stream of pill packets;
determining a medication dosage schedule for a user by processing data received from the optical scanning device scanning the scannable code disposed on the stream of pill packets;
displaying an indication to the user, using the indicator lights, the indication instructing the user to extract one or more pill packets of the stream of pill packets from the medication adherence and monitoring system based on the medication dosage schedule for the user;
detecting a status of extraction of one or more pill packets by processing data received from the optical scanning device scanning the scannable code disposed on the stream of pill packets before, during, or after extraction, wherein each pill packet has its own instance of the scannable code;
providing feedback to the user, using the indicator lights, regarding the status of extraction of the one or more pill packets; and
determining and recording a status of compliance with the dosage schedule based on the status of extraction of the one or more pill packets of the stream of pill packets detected to have passed by the optical scanning device and been extracted through the opening of the housing.

21. The method of claim 20, wherein installing the medication adherence and monitoring system on a medication reservoir that stores a stream of pill packets comprises:
inserting a first packet of the stream of pill packets into the opening on the underside surface of the housing and into the gate; and mounting the housing on the medication reservoir so that the flanges engage the medication reservoir.

22. The method of claim 20, further comprising generating a message sent to a personal electronic device of the user.

23. The method of claim 22, where generating a message comprises:
sending a message, using the wireless transponder, to a remote server requesting that a message be sent to the personal electronic device of the user.

24. The method of claim 23, wherein the remote server sends a message to the personal electronic device of the user.

25. The method of claim 20, wherein providing feedback comprises one or more of:
providing an indication that the user is to continue extracting the one or more pill packet;
providing an indication that the user is near completion of extracting the one or more pill packets; and
providing an indication that the user should stop extracting the one or more pill packets.

26. The method of claim 20, further comprising:
sending the status of compliance to a remote server using the wireless transponder.

27. The method of claim 20, further comprising:
generating a message sent to a caregiver for the user.

28. The method of claim 20, wherein determining a medication dosage schedule for a user further comprises:
receiving an update about the medication dosage schedule from a remote server.

29. The method of claim 20, wherein determining and recording a status of compliance with the dosage schedule further comprises:
sending the status of compliance to a remote server.

30. The method of claim 29, wherein the remote server analyzes the status of compliance and adjusts one or more of:
the medication dosage schedule; and
the compliance status.

\* \* \* \* \*